United States Patent [19]

Burke

[11] Patent Number: 5,021,410

[45] Date of Patent: Jun. 4, 1991

[54] COMBINATIONS OF SELECTIVE ALPHA-ADRENERGIC AGONISTS AND ANTAGONISTS USEFUL IN LOWERING INTRAOCULAR PRESSURE

[75] Inventor: James A. Burke, Tustin, Calif.

[73] Assignee: Allergan, Inc., Irvine, Calif.

[21] Appl. No.: 354,969

[22] Filed: May 22, 1989

[51] Int. Cl.$^5$ .............................................. A61K 31/55
[52] U.S. Cl. ..................................... 514/213; 514/212
[58] Field of Search ................................ 514/213, 212

[56] References Cited

U.S. PATENT DOCUMENTS 4,496,558  1/1985  Demarinis et al. ................. 514/213

OTHER PUBLICATIONS

Chem. Abst. 104:45623n (1986), Van Pinxteren.

Primary Examiner—Stanley J. Friedman
Assistant Examiner—Zohreh A. Fay
Attorney, Agent, or Firm—Martin A. Voet; Howard R. Lambert

[57] ABSTRACT

Methods and pharmaceutical formulations of alpha$_2$ agonists and alpha$_3$ antagonists which are useful in lowering intraocular pressure (IOP) and treatment of intraocular hypertension. Co-administration of a therapeutic amount of alpha$_2$ agonist with a potentiating amount of alpha$_3$ agonist is effective in lowering IOP and treatment of intraocular hypertension.

10 Claims, 1 Drawing Sheet

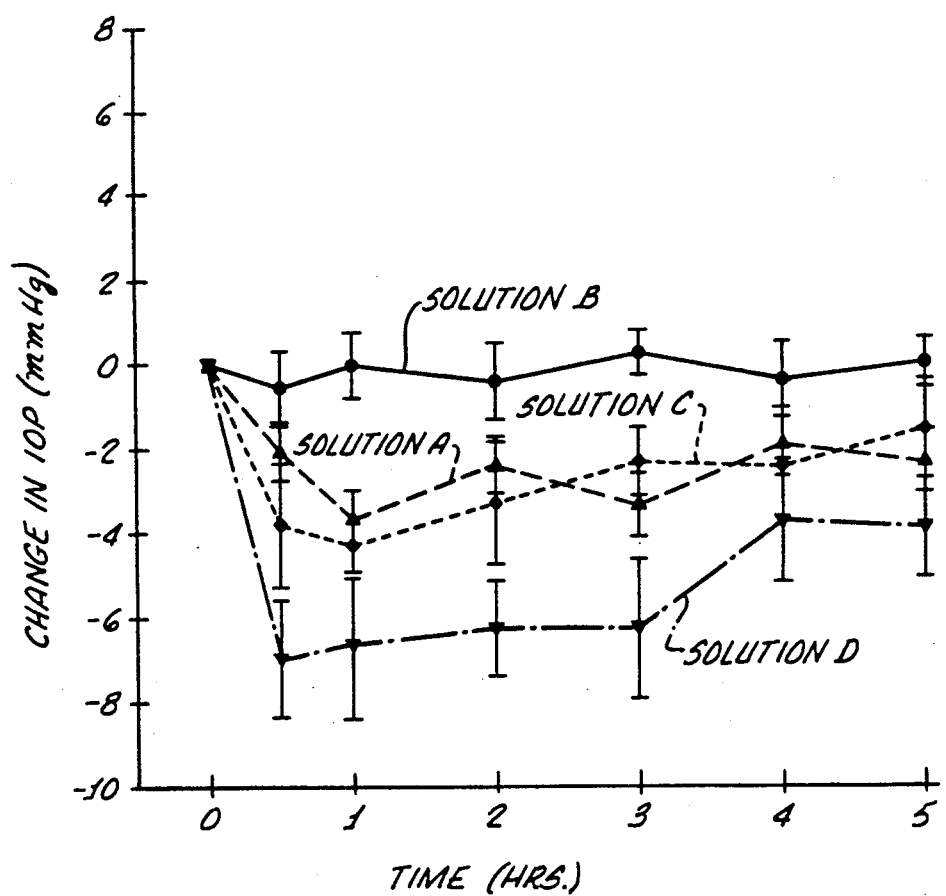

COMBINATIONS OF SELECTIVE ALPHA-ADRENERGIC AGONISTS AND ANTAGONISTS USEFUL IN LOWERING INTRAOCULAR PRESSURE

FIELD OF THE INVENTION

This invention relates to combinations of $alpha_2$ adrenoceptor agonists and $alpha_3$ adrenoceptor antagonists useful in lowering intraocular pressure.

BACKGROUND OF THE INVENTION

Glaucoma is a disease of the eye characterized by increased intraocular pressure. The intraocular pressure (IOP) in the hypertensive eye causes atrophy and excavation of the ocular nerve thereby producing the visual defects associated with glaucoma. If untreated, increased IOP may cause permanent visual defects or even blindness. It is known that IOP may be affected by application of various adrenergic agents which are active on the sympathoadrenal system. Adrenergic agents exert their activity by interaction with adrenal receptors (adrenoceptors). The agents may be characterized by their activity, i.e. as stimulating agents (agonists) or blocking agents (antagonists), and by the specific type of adrenoceptors upon which they act.

Adrenoceptors are of two primary types: alpha and beta. Based upon the selectivity of the receptors for a series of agonists and antagonists, the alpha adrenoceptors are divided into subtypes, designated $alpha_1$, $alpha_2$, and more recently, $alpha_3$.

$Alpha_1$ and $alpha_2$ adrenoceptors were originally described by their anatomical location. The $alpha_1$ and $alpha_2$ adrenoceptors are usually located on post- and pre-junctional sites, respectively. Ever increasing evidence caused a revision of this classification. The $alpha_1$ adrenoceptor is now described as prazosin-sensitive and the $alpha_2$ adrenoceptor as rauwolscine-sensitive.

The existence of a third adrenoceptor is supported by a large amount of experimental evidence. Experiments using selective agonists and antagonists of both $alpha_1$ and $alpha_2$ adrenoceptors demonstrated that in addition to the classical post-junctional $alpha_1$ adrenoceptor, an additional post-junctional adrenoceptor was present which closely resembled the pre-junctional $alpha_2$ adrenoceptor which had been characterized in many systems. The concept of post-junctional $alpha_2$ adrenoceptors mediating prazosin-resistant vasoconstriction has been proposed by Timmermans, et al., *Nauyn-Schmiedeberg's Arch. Pharmacol.*, 310, 189 (1979), and Ruffolo, *Pharm. Biochem. and Behav.*, 22, 827 (1985). It has now been discovered that the prazosin-insensitive post-junctional adrenoceptor is pharmacologically distinct from the pre-junctional $alpha_2$ andrenoceptor. (Ruffolo, R., et al., *Nauyn-Schmiedeberg's Arch. Pharmacol.* 336, 415–418. (1987)) This post-junctional, prazosin-insensitive receptor is referred to as the $alpha_3$ adrenoceptor.

At this juncture, it should be noted that alpha agonists and alpha antagonists appear to preferentially stimulate or block each type of adrenoceptor with varying degrees of specificity rather than exclusively stimulating or blocking one adrenoceptor sub-type. For example, clonidine preferentially stimulates $alpha_2$ adrenoceptor $\geq alpha_3$ adrenoceptor $>> alpha_1$ adrenoceptor and is therefore characterized as an $alpha_2$ agonist. As a further example, an $alpha_3$ antagonist of the present invention, 9-(3methyl-2-butenyloxy)-6-chloro-3-methyl-2,3,4,5-tetrahydro-1H-3 benzazepine, blocks the $alpha_3$ adrenoceptor $\geq alpha_1$ adrenoceptor $>> alpha_2$ adrenoceptor and is therefore characterized as an $alpha_3$ adrenoceptor antagonist.

Topically administered alpha agonists which are efficacious in lowering IOP are part of current ocular hypertension therapy, including glaucoma therapy. However, some undesirable side effects are associated with the use of these compounds for treatment of ocular hypertension. For example, some alpha agonists are known to cause significant and undesirable cardiovascular (systemic) hypotension and mydriasis (pupil dilation). These side effects are mediated by central nervous system $alpha_2$ adrenoceptors and ocular $alpha_1$ adrenoceptors, respectively.

However, based on the known efficacy of some $alpha_2$ agonists for treatment of ocular hypertension, efforts are being made to develop more selective $alpha_2$ adrenoceptors which remain localized in the ocular environment and have less side effects and to develop methods and compositions to potentiate the effect of the agonist while reducing the side effects associated with its use.

To develop either more selective $alpha_2$ agonists or potentiating compositions and methods, it is important to focus on some factors which mediate the efficacy of $alpha_2$ agonists for lowering IOP. The ocular hypotensive activity of an $alpha_2$ agonist is dependent on several factors: (a) the degree of specificity for the $alpha_2$ adrenoceptor, (b) the dosage of the $alpha_2$ agonist and (c) the drug delivery method. The dosage of conventional $alpha_2$ agonists needed to achieve a desired therapeutic ocular hypotensive effect may cause various undesirable side effects, such as cardiovascular hypotension and mydriasis. Depending on the patient, other localized or systemic adverse indications, reactions, or toxicity may result. Accordingly, a need exists for compositions and/or methods which enable either (a) improved therapeutic effect per unit dose of the $alpha_2$ agonist and/or (b) use of smaller doses of the $alpha_2$ agonist.

The present invention is directed to the discovery that co-administrating an $alpha_3$ antagonist with an $alpha_2$ agonist directly to the eye potentiates the IOP lowering effect of the $alpha_2$ agonist. Co-administrating an $alpha_3$ antagonist mitigates, reduces or eliminates undesirable side effects associated with conventional $alpha_2$ agonist therapy for treatment of ocular hypertension and enables treatment with lower $alpha_2$ agonist dosages. In addition, co-administration of an $alpha_2$ agonist with an $alpha_3$ antagonist enables equivalent or improved therapeutic treatment of ocular hypertension as compared to using equivalent or higher dosages of the $alpha_2$ agonist alone.

$Alpha_3$ antagonists, such as those disclosed herein, are known to be useful in treatment of cardiovascular hypertension as disclosed in U.S. Pat. No. 4,683,229 by DeMarinis, et. al. However, $alpha_3$ antagonists have never been used for treatment of ocular hypertension.

SUMMARY OF THE INVENTION

The invention resides in the discovery that co-administrating an $alpha_2$ agonist with a potentiating amount of $alpha_3$ antagonist lowers intraocular pressure (IOP) and is useful in the treatment of ocular hypotension.

The present invention relates to a method for lowering intraocular pressure (IOP) comprising co-administrating to the eye of a mammal suffering from ocular hypertension a therapeutic amount of alpha$_2$ agonist and alpha$_3$ antagonist wherein the amount of alpha$_3$ antagonist potentiates the ocular hypotensive effect of the alpha$_2$ agonist.

The present invention further relates to an ophthalmically acceptable formulation for lowering intraocular pressure (IOP) comprising an ophthalmically therapeutic amount of alpha$_2$ agonist and alpha$_3$ antagonist in an amount which potentiates the ocular hypotensive effect of the alpha$_2$ agonist.

DETAILED DESCRIPTION OF THE INVENTION

Co-administration refers to administering compounds of the present invention serially, or at substantially the same time or simultaneously. Co-administration includes administering the compounds of the present invention separately but at substantially the same time, or administering them at the same time in one pharmaceutical preparation. Serial administration includes administering the compounds of the present invention one after the other wherein the time between administration of the compounds is one hour or less.

An ophthalmically acceptable formulation refers to a formulation comprising an alpha$_2$ agonist and/or an alpha$_3$ antagonist in a suitable carrier comprised of one or more ophthalmically suitable excipients.

Alpha$_2$ agonist, as used herein, refers to compounds that preferentially stimulate alpha$_2$ adrenoceptor and exhibit a hypotensive effect in lowering intraocular pressure. alpha$_3$ antagonist, as used herein, refers to compounds which preferentially block alpha$_3$ adrenoceptors.

Potentiating effect, resulting from co-administration of an ophthalmically acceptable formulation comprising an alpha$_2$ agonist and/or an alpha$_3$ antagonist, refers to decreasing the time for onset of hypotensive effect of the combination, decreasing or eliminating the unwanted initial hypertensive activity of an alpha$_2$ agonist which occurs in some mammals but is not observed in humans, increasing the hypotensive effect over that observed using just an alpha$_2$ agonist, or reducing side effects associated with an alpha$_2$ agonist by enabling use of relatively smaller dosages of an alpha$_2$ agonist in treatment of ocular hypertension.

The alpha$_2$ agonists of the present invention exhibit hypotensive activity in lowering IOP. It is contemplated that any alpha$_2$ agonist which exhibits hypotensive activity can be used in this invention. The preferred alpha$_2$ agonists of the present invention are derived from imidazolidines and their tautomers and azepines.

Preferred imidazolidine-derived alpha$_2$ agonists of the present invention are represented by the tautomeric formulae below:

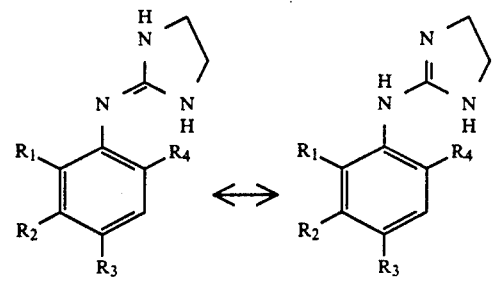

where $R_1$ and $R_2$ are independently hydrogen, $C_{1-6}$ alkyl, fluoro, chloro, bromo or trifluoromethyl, one of $R_3$ and $R_4$ are hydrogen and the other is hydroxy, —N($R_5R_7$), —COOR$_3$, —CON($R_5R_6$), —NR$_5$COR$_6$, $R_5$ and $R_6$ are independently hydrogen or $C_{1-6}$ alkyl, $R_7$ is hydrogen, $C_{1-6}$ alkyl, 2-hydroxyethyl, 2-hydroxypropyl or 3-hydroxypropyl, the sum of the carbon atoms in $R_5$ and $R_6$ or $R_7$ and $R_8$ being twelve or less or —CH$_2$OH, —CN, —OH, —OCOR$_8$, —COCH$_3$, —C(CH$_3$)NOH, —CHNOH, $R_8$ is a $C_{1-6}$ alkyl; or where $R_1$ is hydrogen, $C_{1-6}$ alkyl, fluoro, chloro, bromo or trifluoromethyl, $R_2$ is hydrogen, $R_3$ is hydroxy, —N($R_9R_{10}$), —NR$_9$COR$_9$, $R_4$ is methyl, chloro, bromo or hydroxy, $R_9$ is hydrogen or $C_{1-6}$ alkyl, $R_{10}$ is hydrogen or $C_{1-6}$ alkyl, $R_7$ is hydrogen, $C_{1-6}$ alkyl, 2-hydorxyethyl, 2-hydorxypropyl or 3-hydroxypropyl, the sum of carbon atoms in $R_9$ and $R_{10}$ being twelve or less; or any pharmaceutically acceptable salts thereof. The alkyl substituents may be straight or branched chain. The preferred alkyl substituents are methyl and ethyl derivatives.

The preparation of most of the imidazolidine-derived compounds described above is disclosed in one or more of the following references which are incorporated herein in their entirety: *Clonidine and Related Analogues, Quantitative Correlations*, B. Rouot, et al., *J. Med. Chem.*, Vol. 19, No. 8; 1049–54(1976); U.S. Pat. No. 4,515,800 by Cavero, et al; and U.S. Pat. No. 3,890,319 by Danielowicz, et al. Other imidazolidine-derived compounds described above may be made using techniques and skills well known in the art.

The most preferred imidazolidine-derived alpha$_2$ agonist compounds are clonidine, p-aminoclonidine, 5-bromo-6-(2-imidazolindine-2-ylamino)quinoxaline, and 2-(3,4-dihydroxyphenylimino)imidazolidine.

Preferred azepine-derived alpha$_2$ agonist compounds of the present invention are represented by the formula:

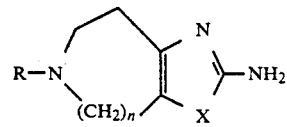

where R is hydrogen, $C_{1-10}$ alkyl, hydroxy substituted $C_{1-20}$ alkyl, phenyl or substituted phenyl; and X is O or S; or any pharmaceutically acceptable salt thereof.

The preparation of these azepine-derived compounds is disclosed in one or more of the following references which are incorporated herein in their entirety: *Oxazolo and Thiozolo Derivatives for Glaucoma Treatment*, K. Thomas, G.m.b.H., Jpn. Kokai Tokyo Koho JP No. 58 46,092 (83 46,092) Mar. 17, 1983; and Offenlegungsschrift No. 2,127,267 Dec. 14, 1972) Bundesrepublik Deutschland. Other azepine-derived compounds described above may be made using techniques and skills well known in the art.

The most preferred azepine-derived alpha$_2$ agonists of the present invention are 2-amino-6-alkyl-4,5,7,8-tetrahydro-6H-thiazolo-(5,4-d)azepine and 2-amino-6-ethyl-4,5,7,8-tetrahydro-6H-oxazolo-(5,4-d)azepine both of which are members of the group of compounds described by the general structure of the azepine-derived compound shown above.

Other alpha$_2$ agonists, such as derived from phenylethylamines, more specifically epinephrine, norepinephrine and dipivalylepinephrine, may be used herein without departing from the scope of the present invention. Preparation of epinephrine, norepinephrine and dipivalylepinephrine are known in the art and they are readily and commerically available. (Epinephrine and norepinephrine are available from Sigma Chemical Co.; dipivalylepinephrine is available from San-Ten or Allergan, Inc.).

It is expected that any alpha$_3$ antagonist can be used in this invention. The preferred alpha$_3$ antagonists are derived from benzazepines. More preferred are the various 6(9)-substituted benzazepine-derived compounds having the formula:

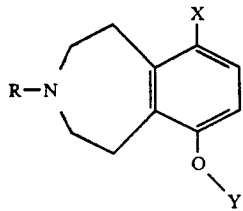

where:
R is $C_{1-5}$alkyl;
X is Br, Cl, or F;
Y is $-CH_2-CH=C(CH_3)_2$, $-CH=CH-CH_3$, $-CH_2-(CH_3)C=CH_2$, $-CH=C(CH_3)_2$, $-CH=CH-CH_2-CH_3$, $-CH=CH-CH(CH_3)_2$; or any pharmaceutically acceptable salt or hydrate thereof.

The most preferred alpha$_3$ antagonist benzazepine-derived compounds are 9-(3-methyl-2-butenyloxy)-6-chloro-3-methyl-2,3,4,5-tetrahydro-1H-3-benzazepine and 9-(1-propenyloxy)-6-chloro-3-methyl-2,3,4,5-tetrahydro-1H-3-benzazepine. These compounds are described by the general benzazepine structure shown above. Preparation of these benzazepine-derived alpha$_3$ antagonists of the present invention is disclosed in U.S. Pat. No. 4,683,229 by DeMarinis, et al. which is incorporated herein in its entirety.

Potentiating the ocular hypotensive effect of an alpha$_2$ agonist by co-administratering an alpha$_2$ agonist and an alpha$_3$ antagonist to a hypertensive eye may focus on one or more aspects of treatment of ocular hypertension, depending on the needs or goals of the treatment and/or management of the patient's ocular hypertension. Potentiating effects include, but are not limited to, decreasing the time for onset of hypotensive effect, decreasing any hypertensive effects, increasing the hypotensive effect of alpha$_2$ agonist, both in a dose responsive manner and over time, and decreasing the side effects which may be associated with the use of the alpha$_2$ agonist by enabling an equivalent therapeutic effect by treatment with an alpha$_2$ agonist and alpha$_3$ antagonist in lower doses.

Doses of an alpha$_2$ agonist in an ophthalmic preparation within the scope of the present invention will comprise an efficacious, non-toxic quantity of the agonist in an ophthalmically pharmaceutically acceptable liquid, gel, cream or an aqueous or nonaqueous liquid suspension or solution. In this regard, the preferred effective dose range of alpha$_2$ agonist having a therapeutic effect in mammals is from about 0.001% to about 1.0% weight/volume. Regardless of the preferred range stated herein, one can determine the most efficacious dose for a particular alpha$_2$ agonist by carrying out a dose response curve as is well known in the art.

Doses of an alpha$_3$ antagonist in ophthalmic preparations within the scope of the present invention will comprise efficacious, non-toxic quantities of alpha$_3$ antagonist which will potentiate the IOP lowering effect of the alpha$_2$ agonist when co-administered therewith.

Therapeutically effective doses of alpha$_2$ agonists and alpha$_3$ antagonists will vary depending on what therapeutic effect is desired or the special needs and idiosyncrasies of the individual patient. Accordingly, a wide range of alpha$_2$ agonist/alpha$_3$ antagonist dose ratios are possible. Preferably, the dose ratio of alpha$_2$ agonist/alpha$_3$ antagonist is about 0.00005/1 to about 100/1. The most preferred dose ratio of alpha$_2$ agonist/alpha$_3$ antagonist is about 0.025/1 to about 100/1. It is possible to determine precise therapeutic dose ratios by carrying out a dose response curve as is well known in the art.

In this regard, the preferred dose range of alpha$_3$ antagonists having a hypotensive potentiating effect in mammals when co-administered with alpha$_2$ agonists is from about 0.01% to about 2.0% weight/volume of alpha$_3$ antagonists to solution.

Ophthalmic preparations having only the alpha$_2$ agonist or the alpha$_3$ antagonist in the preferred dose ranges may be prepared. However, it is preferred to make ophthalmic preparations having both the alpha$_2$ agonist and the alpha$_3$ antagonist for the convenience of the patient.

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount (% w/v) |
|---|---|
| alpha$_2$ agonist[1] | about 0.0001 to about 1.0 |
| alpha$_3$ antagonist[1] | about 0.01 to about 2.0 |
| Preservative[2] | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100%. |

In Table I above, the superscript numeral one refers to the fact that separate alpha$_2$ agonist or alpha$_3$ antagonist preparations may be made by not including either the alpha$_3$ antagonist or alpha$_2$ agonist respectively. Whereas the superscript numeral two refers to the fact that an unpreserved unit dose formulation does not contain preservative.

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in the ophthalmic preparation of the present invention. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particulary sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include, but are not limited to, acetate buffers, citrate buffers, phosphate buffers, and borate buffers. Acids or bases may be used to adjust the pH of these formulations as needed.

In a similar vein, an ophthalmically acceptable antioxidant for use in the present invention includes, but is not limited to sodium metabisulfite, sodium thiosulfate, acetylcysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

A useful formulation for an ophthalmic preparation comprising the present invention is shown below in Table II.

TABLE II

| Ingredient | Amount (% w/v) |
| --- | --- |
| alpha$_2$ agonist | about 0.0001 to about 1.0 |
| alpha$_3$ antagonist | about 0.01 to about 2.0 |
| Benzalkonium Chloride | 0–0.10 |
| Polyvinyl Alcohol (Grade 20–90) | 0–40 |
| Sodium Chloride | 1–10 |
| Sodium Citrate, Dihydrate | 0.01–10 |
| Citric Acid, Monohydrate | 0.01–2 |
| Purified Water | q.s. to make 100% |

EXPERIMENTAL

Ocular co-administration of an alpha$_2$ agonist and an alpha$_3$ antagonist to effect lowering of IOP was experimentally tested in two animal models, namely the New Zealand White rabbit and the Capuchin monkey. In both experimental models, co-administrating an alpha$_2$ agonist and an alpha$_3$ antagonist demonstrated significant potentiation of the ocular hypotensive effect of the alpha$_2$ agonist.

EXAMPLE 1

The effect of co-administrating of alpha$_2$ agonists and alpha$_3$ antagonists on lowering IOP was tested in New Zealand White rabbits with normotensive IOP and weighing 3–4 kgs. Topical anesthesia was produced by instillation of about 5 $\mu$l of 0.05% proparacaine.HCl, an ophthalmic anaesthetic, into the lower conjunctival sac of each eye.

Separate solutions of various alpha$_2$ agonists and an alpha$_3$ antagonist were prepared by dissolving the specified quantity of agonists or the antagonist in distilled water to obtain the concentrations shown below in Table III. The pH of the final solutions ranged from about 4 to about 7.5 as indicated by the characteristics of the individual drugs.

TABLE III

| | Concentration (% w/v) |
| --- | --- |
| alpha$_2$ Agonist | |
| Clonidine | 0.03 |
| p-aminoclonidine | 0.1 |
| 2-(3,4-dihydroxyphenyl-imino)imidazolidine | 0.03 |
| 5-bromo-6-(2-imidazolidine-2-ylamino)quinoxaline | 0.1 |
| 2-amino-6-allyl-4,5,7,8-tetrahydro-6H-thiazolo-(5,4-d)azepine | 0.03 |
| 2-amino-6-ethyl-4,5,7,8-tetrahydro-6H-oxazolo-(5,4-d)azepine dihydrochloride | 1 |
| alpha$_3$ Antagonist | |
| 9-(3methyl-2-butenyloxy)-6-chloro-3-methyl-2,3,4,5-tetrahydro-1H-3-benzazepine | 1 |

At time zero, intraocular pressure (IOP) and pupil diameter (PD) were both measured in both eyes for each animal. IOP was measured using a DIGILAB ® pneumatonograph and PD was measured using an OP-TISTICK ® ocular ruler to the nearest 0.5 mm. Immediately following the baseline reading for each animal, 50 $\mu$l of the alpha$_3$ antagonist solution was instilled into the lower conjunctival sac of the test eye of the animal, with the contralateral eye receiving 50 $\mu$l of saline in the lower conjunctival sac as a control. Thirty minutes after application of the alpha$_3$ antagonist, IOP and PD were again measured for each eye. Immediately following these measurements, about 50 $\mu$l of one of the alpha$_2$ agonists solution given in Table III was administered to the test eye in the same manner described above. Thereafter, IOP and PD measurements for each eye of each animal were made at 30 minutes after administration of the alpha$_2$ agonist, then hourly for 6 hours. In a control experiment, the animals were treated and tested as described above except that no animal received the alpha$_3$ antagonist, 9-(3-methyl-2-butenyloxy)-6-chloro-3-methyl-2,3,4,5-tetrahydro-1H-3-benzazepine, which is designated as Y in Table IV.

The results of these experiments at 30 minutes and 2 hours after administration of the alpha$_2$ agonists are shown in Table IV, and Table V, respectively, with the data expressed as the mean changes from baseline values. Note that in rabbits, alpha$_2$ agonists of the imidazolidine class increase IOP up to 1 hour after drug application then decrease IOP maximally after 2 hours.

TABLE IV

| | Δ IOP (mm Hg) at 0.5 hour | | |
|---|---|---|---|
| Alpha₂ Agonist | Alpha Agonist (A) | co-administration of alpha₂ agonist and alpha₃ antagonist (A + Y) | A − (A + Y) |
| Clonidine | +4.8 | −4.1 | −8.9 |
| p-aminoclonidine | +2.3 | −3.3 | −5.6 |
| 2-(3,4-dihydroxyphenyl-imino)imidazolidine | +4.4 | −1.5 | −5.9 |
| 5-bromo-6-(2-imidazoline-2-ylamino)quinoxaline | +1.0 | −4.6 | −5.6 |
| 2-amino-6-allyl-5,6,7,8 tetrahydro-6H-thiazolo-(4,5-d)-azepine | −1.2 | −5.2 | −4.0 |
| 2-amino-6-ethyl-4,5,7,8-tetrahydro-oxazolo (5,4-d)-azepine dihydrochloride | −0.6 | −6.4 | −5.8 |

TABLE V

| | Δ IOP (mm Hg) at 2 hours | | |
|---|---|---|---|
| Alpha₂ Agonist | Alpha Agonist (A) | co-administration of alpha₂ agonist and alpha₃ antagonist (A + Y) | A − (A + Y) |
| Clonidine | +1.3 | −3.1 | −4.1 |
| p-aminoclonidine | +0.2 | +0.7 | +0.5 |
| 2-(3,4-dihydroxyphenyl-imino)imidazolidine | +2.0 | +2.5 | +0.5 |
| 5-bromo-6-(2-imidazoline-2-ylamino)quinoxaline | −3.0 | −5.7 | −2.7 |
| 2-amino-6-allyl-5,6,7,8 tetrahydro-6H-thiazolo (4,5-d)-azepine | −1.1 | −2.1 | −1.0 |
| 2-amino-6-ethyl-4,5,7,8-tetrahydro-oxazolo-(5,4-d)-azepine dihydrochloride | −2.1 | −2.4 | −0.3 |

Table IV shows that the hypertensive effect of the imidazoline alpha₂ agonist was significantly reversed by a 30 minute pretreatment with the designated alpha₃ antagonist. The small hypotensive effect of the azepine alpha₂ agonists was also potentiated by the alpha₃ antagonist. Table V shows that 2 hours after agonist administration some potentiation of the hypotensive effect could be observed. The alpha₃ antagonist by itself exhibited no significant hypotensive effect.

These data demonstrate that the serial co-administration of alpha₃ antagonist and the alpha₂ agonists (30 minutes later) resulted in a substantial and significant lowering of IOP over treatment with only the alpha₂ agonists above. Additionally, pretreatment with the alpha₃ antagonist reversed the transient hypertensive effect of some alpha₂ agonists.

EXAMPLE 2

The effect of co-administrating an alpha₂ agonist and an alpha₃ antagonist was tested in Capuchin monkeys as follows. Capuchin monkeys with normotensive IOP were sedated by intramuscular injection of about 1 mg/kg ketamine into the thigh. One drop of 0.05% proparacaine. HCl was applied onto the cornea of each eye. To hold the monkey's eye open for intraocular pressure (IOP) and pupil diameter (PD) measurements, each eye was fitted with an eye speculum. Several solutions containing both the alpha₂ agonist and an alpha₃ antagonist, or alpha₂ agonist alone or alpha₃ antagonist alone were prepared by dissolving a specified quantity of the agonist or antagonist in distilled water to obtain the concentration shown below in Table VI. The pH of the final solutions ranged from about 4.5 to about 7.5, depending on the particular formulation.

TABLE VI

| | Concentration (% w/v) |
|---|---|
| Solution A | |
| alpha₂ agonist[1] | 0.1 |
| Solution B | |
| alpha₃ antagonist[2] | 1 |
| Solution C | |
| alpha₂ Agonist[1] | 0.1 |
| alpha₃ Antagonist[2] | 0.3 |
| Solution D | |
| alpha₂ Agonist[1] | 0.1 |
| alpha₃ Antagonist[2] | 1 |

[1]5-bromo-6-(2-imidazoline-2-ylamino)quinoxaline
[2]9-(3-methyl-2-butenyloxy)-6-chloro-3-methyl-2,3,4,5-tetrahydro-1H-3-benzazepine At time zero, IOP and PD were measured for both eyes of each animal as indicated in Example 1. Immediately following the baseline reading for each animal, about 50 μl of solution A, B, C, or D was placed in the test eye of the animal with the contralateral eye receiving an equivalent amount of saline. Thereafter, IOP and PD measurements were made at 30 minutes, 1 hour and at each hour thereafter through up to 5 hours. The results of these experiments are summarized below in the figure with the data expressed as the mean changes from baseline values.

The FIGURE shows the ipsilateral effects of a single drop (so μl) of Alpha₂ Agonist and Alpha₃ Antagonist in normotensive Capuchin monkeys.

The FIGURE that the hypotensive effect of the alpha₃ antagonist, when used alone, was negligible. However, the hypotensive effect of the alpha₂ agonist was significantly potentiated by co-administrating in the same solution of the alpha₂ agonist and alpha₃ antagonist. This potentiation was dose-related because the hypotensive effect of alpha₂ agonist was further augmented by increasing the ratio of alpha₂ agonist/alpha₃ antagonist from ⅓ to 1/10.

I claim:

1. A method for lowering intraocular pressure (IOP) comprising co-administrating to the eye of a mammal suffering from ocular hypertension a therapeutic amount of alpha₂ agonist and alpha₃ antagonist wherein the amount of alpha₃ potentiates the ocular hypotensive effect of the alpha₂ agonist.

2. A method according to claim 1, wherein the ratio of alpha₂ agonist to alpha₃ antagonist is 0.00005/1 to about 100/1.

3. A method according to claim 2, wherein the ratio of alpha₂ agonist to alpha₃ antagonist is 0.025/1 to 25/1.

4. A method according to claim 1 wherein said alpha₂ agonist is epinephrine, norepinephrine or dipivalylepinephrine and said alpha₃ antagonist is a compound of the formula:

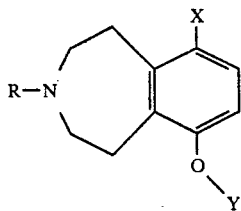

wherein:
R is C₁₋₅alkyl;
X is Br, Cl, or F;
Y is —CH₂—CH=C(CH₃)₂, —CH=CH—CH₃, —CH₂—(CH₃)C=CH₂, —CH=C(CH₃)₂, —CH=CH—CH₂—CH₃), —CH=CH—CH(CH₃)₂; or a pharmaceutically acceptable salt or hydrate thereof.

5. A method according to claim 4 wherein said alpha₃ antagonist is 9-(1-propenyloxy)-6-chloro-3-methyl-2-3,4,5-tetrahydro-1H-3-benzazepine or 9-(3-methyl-2-butenyloxy)-6-chloro-3-methyl-2,3,4,5-1H-3-benzazepine.

6. An ophthalmically acceptable formulation for lowering intraocular pressure (IOP) comprising a therapeutic amount of alpha₂ agonist and alpha₃ antagonist in an amount which potentiates the ocular hypotensive effect of the alpha₂ agonist in a pharmaceutically acceptable excipient.

7. A formulation according to claim 6, wherein the ratio of alpha₂ agonist to alpha₃ antagonist is 0.00005/1 to about 100/1.

8. A formulation according to claim 7, wherein the ratio of alpha₂ agonist to alpha₃ antagonist is 0.025/1 to 25/1.

9. A formulation according to claim 8 wherein said alpha₂ agonist is epinephrine, norepinephrine or dipivalylepinephrine and said alpha₃ antagonist is a compound of the formula:

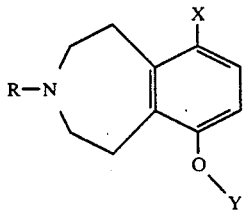

wherein:
R is C₁₋₅alkyl;
X is Br, Cl, or F;
Y is —CH₂—CH=C(CH₃)₂, —CH=CH—CH₃, —CH₂—(CH₃)C=CH₂, —CH=C(CH₃)₂, —CH=CH—CH₂—CH₃, —CH=CH—CH(CH₃)₂; or a pharmaceutically acceptable salt or hydrate thereof.

10. A formulation according to claim 9 wherein said alpha₃ antagonist is 9-(1-propenyloxy)-6-chloro-3-methyl-2-3,4,5-tetrahydro-1H-3-benzazepine or 9-(3-methyl-2-butenyloxy)-6-chloro-3-methyl-2,3,4,5-1H-3-benzazepine.

* * * * *